United States Patent
Nagy et al.

(10) Patent No.: US 10,017,484 B2
(45) Date of Patent: Jul. 10, 2018

(54) CATALYSTS CONTAINING SPECIFIC TITANIUM POLYMORPHIC FORMS

(71) Applicant: Lyondell Chemical Technology, L.P., Houston, TX (US)

(72) Inventors: Sandor Nagy, Webster, TX (US); Barbara Kimmich, Houston, TX (US); Xueyong Yang, Bellaire, TX (US); Jenny M. Oran Osment, Humble, TX (US); Debra L. Jackson, Huffman, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 15/353,998

(22) Filed: Nov. 17, 2016

(65) Prior Publication Data

US 2017/0158655 A1 Jun. 8, 2017

Related U.S. Application Data

(60) Provisional application No. 62/262,089, filed on Dec. 2, 2015.

(51) Int. Cl.
| | | |
|---|---|---|
| *B01J 23/00* | (2006.01) | |
| *C07D 301/19* | (2006.01) | |
| *B01J 21/06* | (2006.01) | |
| *B01J 21/08* | (2006.01) | |
| *B01J 35/10* | (2006.01) | |
| *B01J 37/02* | (2006.01) | |
| *B01J 37/08* | (2006.01) | |
| *B01J 37/06* | (2006.01) | |

(52) U.S. Cl.
CPC .......... *C07D 301/19* (2013.01); *B01J 21/063* (2013.01); *B01J 21/08* (2013.01); *B01J 35/1023* (2013.01); *B01J 35/1047* (2013.01); *B01J 37/0217* (2013.01); *B01J 37/0236* (2013.01); *B01J 37/06* (2013.01); *B01J 37/08* (2013.01)

(58) Field of Classification Search
CPC ..... C07D 301/19; B01J 37/0236; B01J 37/06; B01J 37/08; B01J 37/0217; B01J 35/1023; B01J 21/08; B01J 21/063; B01J 21/1047
USPC .......................................... 549/529; 502/350
See application file for complete search history.

(56) References Cited

U.S. PATENT DOCUMENTS

2007/0260074 A1 11/2007 Buijink et al.

OTHER PUBLICATIONS

Wikipedia ,Titanium dioxide, Sep. 2014, p. 1-15.*
Lafond et al, Non-hydrolytic sol-gel routes based on alkyl halide elimination: toward better mixed oxide catalysts and new supports Application to the preparation of a SiO2—TiO2 epoxidation catalyst, Journal of Molecular Catalysis A: Chemical 182-183, p. 81-88. (Year: 2002).*
The International Search Report and Written Opinion for PCT/US2016/062537 dated Feb. 21, 2017.

* cited by examiner

*Primary Examiner* — Taylor V Oh (57) ABSTRACT

A catalyst composition which comprises titanium, wherein part of the titanium is present as a titanium dioxide phase and at least some of the titanium dioxide phase is in the brookite polymorphic form is provided. In some embodiments, the catalyst also comprises a silica support which exhibits a high surface area and pore volume. Methods of preparing the catalyst and its use in an epoxidation reaction are also provided.

19 Claims, 1 Drawing Sheet

US 10,017,484 B2

CATALYSTS CONTAINING SPECIFIC TITANIUM POLYMORPHIC FORMS

CROSS-REFERENCE TO RELATED APPLICATIONS

This application claims the benefit of priority to U.S. Provisional Application No. 62/262,089, filed on Dec. 2, 2015, which is incorporated herein by reference in its entirety.

FIELD OF THE INVENTION

The present disclosure relates to chemical catalysts, including their use in olefin epoxidation. In some aspects, the present disclosure also provides methods of using the catalysts to prepare an epoxide.

BACKGROUND OF THE INVENTION

Catalysts are important components of many chemical manufacturing processes, and may be used to accelerate the rate of the reaction and/or to increase the selectivity or efficiency towards the desired product(s). Catalysts can find a wide range of utilizations in different chemical reactions. The catalytic epoxidation of olefins with oxygen is an industrially useful process for preparing compounds such as ethylene oxide and propylene oxide. Catalyst compositions, such as titanated silica catalysts, have been used to catalyze the reaction of alkenes with hydroperoxides to produce corresponding epoxides. Catalyst compositions which exhibit improved activity or peroxide conversion are commercially attractive. Providing new catalyst compositions and new methods that exhibit improvements in one or more properties and/or reaction parameters remains an important goal.

SUMMARY OF THE INVENTION

In one aspect, the present disclosure provides catalyst compositions comprising: (a) titanium, wherein a part of the titanium is present as titanium dioxide phase and at least 0.1 wt. % of the titanium dioxide phase is in a brookite form; and (b) a silica support, wherein the titanium has been deposited on the silica support. In some embodiments, the brookite form of titanium dioxide phase is present in an amount from about 0.1 wt. % to about 50 wt. % of the titanium dioxide phase. In some embodiments, the catalyst compositions have powder X-ray diffraction spectra comprising peaks at about 25.3, 25.7, 30.8, 36.1, and 48.0 °2θ. In some embodiments, the silica support of the catalyst compositions comprise amorphous silica having: (a) a surface area greater than 800 m$^2$/g; and (b) a pore volume greater than 1.0 cm$^3$/g. In some embodiments, the amount of titanium dioxide is from about 1 wt. % to about 8 wt. % of the catalyst compositions. In some embodiments, the catalyst compositions further comprise a plurality of organosilicate$_{(C≤24)}$ groups on the surface of the catalyst composition. In some embodiments, the organosilicate$_{(C1-24)}$ group is —OSi(CH$_3$)$_3$.

In some aspects, the present disclosure provides methods comprising (a) obtaining a silica support, wherein the silica support comprises amorphous silica having a surface area greater than 800 m$^2$/g and a pore volume of greater than 1.0 cm$^3$/g; (b) drying the silica support to produce a dried silica support; (c) depositing a titanium-containing reagent on the dried silica support to produce a titanium-treated silica support; (d) calcining the titanium-treated silica support to produce a titanated silica support; and (e) washing the titanated silica support with water or an alcohol$_{(C1-12)}$ to form a washed titanated silica support; whereby the methods produces catalyst compositions, wherein at least 0.1 wt. % of the titanium dioxide phase is in a brookite form. In some embodiments, the silica support is dried at a temperature from about 100° C. to about 850° C. for a time period from about 1 hour to about 48 hours. In some embodiments, the titanium-containing reagent is titanium (IV) alkoxide, titanium (IV) halide, or a mixed titanium (IV) alkoxide halide. In some embodiments, the titanium (IV) halide is TiCl$_4$. In some embodiments, the TiCl$_4$ is deposited to the dried silica support as a liquid, as a gas, or as part of a solution, wherein the solution further comprises an aromatic or aliphatic solvent. In some embodiments, the titanium-containing reagent is deposited in the vapor phase at temperature from about 25° C. to about 800° C. In some embodiments, the titanium-treated silica support is calcined at a temperature from about 300° C. to about 800° C. In some embodiments, the methods further comprise drying the washed titanated silica support. In some embodiments, the methods further comprise reacting the washed titanated silica support with a silylating agent. In some embodiments, the silylating agent is hexamethyldisilazane.

In some aspects, the present disclosure provides methods of preparing an epoxide comprising: (a) admixing an olefin$_{(C2-12)}$ and an oxidizing agent to form a reaction mixture; and (b) contacting the olefin$_{(C2-12)}$ and oxidizing agent with a catalyst composition described herein under conditions sufficient to produce an epoxide$_{(C2-12)}$. In some embodiments, the oxidizing agent is an organic hydroperoxide. In some embodiments, the organic hydroperoxide is tert-butyl hydroperoxide, cumene hydroperoxide, or ethylbenzene hydroperoxide. In some embodiments, the olefin is propylene.

While multiple embodiments are disclosed, still other embodiments will become apparent to those skilled in the art from the following detailed description. As will be apparent, certain embodiments, as disclosed herein, are capable of modifications in various aspects, all without departing from the spirit and scope of the claims as presented herein. Accordingly, the examples and detailed description are to be regarded as illustrative in nature and not restrictive.

BRIEF DESCRIPTION OF THE DRAWING

The following figures illustrate certain embodiments of the subject matter disclosed herein. The claimed subject matter may be better understood by referring to the following description taken in conjunction with the accompanying figures, in which like reference numerals identify like elements.

DETAILED DESCRIPTION OF THE INVENTION

In some aspects, the present disclosure provides a titanated silica catalyst which contains titanium in the brookite polymorphic form along with other more common polymorphs of titania—rutile and anatase. In some embodiments, some of the titanium is present in both the brookite polymorphic form and at least one of either the rutile or the anatase polymorphic form besides other forms not detected by powder X-ray diffraction (XRD) method. In some embodiments, the titanium on the catalyst comprises a reduced amount of rutile and/or anatase polymorphic form and increased brookite polymorphic form. In some embodiments, the catalyst comprises a silica support which has both a high surface area and a high pore volume. The present disclosure also provides methods of using these catalysts for the epoxidation of alkenes and aralkenes.

I. CATALYST COMPOSITION

In some embodiments, the present disclosure relates to a catalyst which may be used to produce an epoxide from an olefin in the presence of an oxidizing agent. In some embodiments, the catalyst contains titanium in the brookite polymorphic form. For example, the catalyst composition may comprise:
  (a) titanium, wherein the titanium comprises titanium oxide phase exhibiting a brookite polymorphic form; and
  (b) a silica support, wherein the titanium has been deposited on the silica support.

In some embodiments, the catalyst composition comprises from about 0.1% to about 50% of the titania phase in the brookite polymorphic form. The titanium in the brookite polymorphic form that is present in the catalyst composition has a powder X-ray diffraction spectra characterized by peaks at 25.3, 25.7, 30.8, 36.1, and 48.0 °2θ. In some embodiments, the silica support comprises amorphous silica having:
  (a) a surface area greater than 800 m$^2$/g; and
  (b) a pore volume greater than 1.0 cm$^3$/g.

In some embodiments, the catalyst comprises from about 1 wt. % to about 8 wt. % deposited titanium. The catalyst compositions may further comprise an organosilicate$_{(C \leq 24)}$ deposited on the titanium. In some embodiments, the organosilicate is hexamethyldisilazane or trimethylsilyl.

In certain embodiments, the silica support of the catalyst further comprises a high surface area. In some embodiments, the surface area of the silica support is greater than 800 m$^2$/g. In some embodiments, the surface area is from about 800 m$^2$/g to about 1200 m$^2$/g. In some embodiments, the surface area is from about 900 m$^2$/g to about 1100 m$^2$/g. In some embodiments, the surface area is from about 910 m$^2$/g to about 970 m$^2$/g. In some embodiments, the surface area is about 950 m$^2$/g. In some embodiments, the surface area is greater than 1000 m$^2$/g.

In some aspects, the silica support of the catalyst further comprises a high pore volume. In some embodiments, the high pore volume is greater than 1.25 g/cm$^3$. In some embodiments, the pore volume is from about 1.25 g/cm$^3$ to about 3.50 g/cm$^3$. In some embodiments, the pore volume is from about 1.5 g/cm$^3$ to about 3.0 g/cm$^3$. In some embodiments, the pore volume is from about 2.0 g/cm$^3$ to about 2.5 g/cm$^3$. In some embodiments, the pore volume is from about 2.20 g/cm$^3$ to about 2.5 g/cm$^3$. In some embodiments, the pore volume is greater than 2.0 g/cm$^3$. The pore volume and surface area may be measured using nitrogen porosimetry.

In some aspects, the silica support of the catalyst further comprises an average pore diameter greater than 70 Å. In some embodiments, the average pore diameter from about 70 Å to about 150 Å. In some embodiments, the average pore diameter is from about 90 Å to about 110 Å. In some embodiments, the average pore diameter is from about 91 Å to about 108 Å. In yet another aspect, the silica support of the catalyst further comprises both a high surface area and a high pore volume. In some embodiments, the silica support has both a high surface area greater than 800 g/cm$^3$ and a high pore volume greater than 1.25 g/cm$^3$. Without being bound any theory, the combination of a high surface area and a high pore volume may assist in producing a high conversion rate of the oxidant into the desired product.

In another aspect, the silica support of the catalyst further comprises a particular particle size. In some embodiments, the silica support is obtained through crushing or extruding. In some embodiments, the crushing or extruding of the silica support allows a particular particle size to be obtained for the silica support. In another embodiment, the particle size of the silica support is obtained by classifying the silica support of the catalyst through a sieve. In some embodiments, the particle size of the silica support is less than about 5.0 mm. In some embodiments, the particle size is from about 0.5 mm to about 3.0 mm. In another aspect, the silica support of the catalyst further comprises depositing a titanium content from about 2 wt. % to about 8 wt. % of the total weight of the catalyst composition. In some embodiments, the titanium content is from about 5 wt. % to about 7 wt. %.

A. Silica Support of the Catalyst

In some aspects, the silica support of the catalyst comprises an inorganic siliceous solid. In some embodiments, the siliceous solid is an amorphous silicon oxide. In some embodiments, the siliceous solid is characterized by a relatively large surface area relative to its mass. In some embodiments, the surface area is greater than 800 m$^2$/g. In some embodiments, the surface area is from about 800 m$^2$/g to about 1200 m$^2$/g. In some embodiments, the silica support comprises one or more open spaces, pores, or interstices within the silicon oxide structure. Some non-limiting examples of silicon oxide which may be used include flocculated or otherwise linked together to form densely packed masses of silica oxide, synthetic silica powders with flocculated in open-packed and readily disintegrated and loosely knit aggregates, or the silica support that may be used includes mixtures including but not limited to silica-alumina, silica-magnesia, silica-zirconia, silica-alumina-boric, and silica-aluminum-magnesia. It is contemplated, that in some embodiments, the silica support is a molecular sieves, including but not limited to, large pore or mesoporous molecular sieves such as MCM-41, MCM-48, and M41S.

In some aspects, the silica support is dried before the silica support is deposited with a transition metal. In some embodiments, drying the silica support comprises heating the silica support to a temperature from about 100° C. to about 850° C. In some embodiments, the temperature is greater than about 120° C. In some embodiments, the temperature is from about 150° C. to about 300° C. In some embodiments, the silica support is dried in a vacuum. In other embodiments, the silica support is dried under a flowing stream of a gas such as nitrogen or a noble gas. In some embodiments, the flowing stream of the gas helps to further drive the silica support. In some aspects, the silica support is dried for a time period from about 1 hour to about 48 hours. In some aspects, the time period is from about 2 hours to 24 hours.

In some embodiments, the silica support of the catalyst comprises silicon oxide. In some embodiments, the silica support also comprises titanium oxide. In some embodiments, the silica support comprises at least 90 wt. % silicon oxide. In some embodiments, the silica support comprises at least 95 wt. % silicon oxide. The percentage of silicon oxide and other oxides in the silica support may be measured using XRF (x-ray fluorescence spectroscopy). In some embodiments, the other oxides comprise less than about 10 wt. % of the silica support. In some embodiments, the other oxides comprise from about 0.01 wt. % to about 9.9 wt. % of the silica support.

In some aspects of the present disclosure, the silica support comprises adsorbed solvents from the process. In some embodiments, the adsorbed solvents are removed through the process of preparing the catalyst. In some embodiments, the silica support comprises less than 3 wt. % of carbon. In some embodiments, the silica support comprises from about 0.05 wt. % to about 3 wt. %. In some embodiments, the silica support comprises from about 1 wt. % to about 2 wt. % of carbon from adsorbed solvent or other materials. In some embodiments, the carbon content of the silica support is measured using carbon nitrogen analysis by converting the carbon into carbon dioxide at a high temperature.

B. Active Components

In some aspects of the present disclosure, the catalyst comprises one or more catalytically active metal compounds as active sites deposited in or on the silica support. In some embodiments, the active components deposited on the silica support are titanium compounds. In some embodiments, the titanium species are deposited using a titanium source. The titanium source that may be used is a titanium alkoxide, a titanium halide, or titanium with mixed alkoxide and halide ligands. In some embodiments, the titanium source is titanium metal in the +3 or +4 oxidation state. In some embodiments, the titanium source is a titanium metal in the +4 oxidation state. In some embodiments, the titanium source is a titanium complex with at least one halide ligand.

In some aspects, the catalyst of the present disclosure comprises from about 0.1 wt. % to about 10 wt. % of titanium in the total weight of the catalyst. In some embodiments, the catalyst comprises about 2 wt. % to about 8 wt. % of titanium in the total weight of the catalyst. In some embodiments, the catalyst comprises from about 5 wt. % to about 7 wt. % titanium in the total weight of the catalyst. In some embodiments, multiple different depositions of titanium are used to obtain the desired amount of titanium on the catalyst.

In some aspects, the titanium deposited on the solid component exhibits one or more polymorphic forms. In some embodiments, the titanium deposited on the solid component exhibits titanium in the brookite polymorphic form. In some embodiments, the titanium deposited on the solid component exhibits the brookite polymorphic form and either the rutile or the anatase polymorphic form. In some embodiments, the titanium deposited on the solid component exhibits the brookite, rutile, and anatase polymorphic forms.

In some aspects, some of the titanium deposited on the silica support can exhibit several polymorphic forms. In some embodiments, part of the titanium deposited on the silica support exhibits titanium in the brookite polymorphic form. The brookite form can be present between 0.1 and 50% of the total titanium (brookite, anatase and rutile combined) as measured by the XRD method. Without wishing to be bound by any theory, one difference between the polymorphs of titania is that $TiO_2$ is packed in different crystalline forms with different dimensions and symmetry, resulting district surface properties of the titania phases.

The terms "brookite", "brookite form" or "brookite polymorphic form" are synonymous and represent a form of titanium oxide, which may be characterized in some embodiments by an orthorhombic crystal system with lattice parameters of 9.2100, 5.4720, and 5.1710 for a, b, and c, respectively and α, β, and γ are each 90°. In some embodiments, the brookite form exhibits an XRD spectra (2θ) comprising peaks at 25.3±0.2 °2θ, 25.7±0.2 °2θ, 30.8±0.2 °2θ, 36.1±0.2 °2θ, and 48.0±0.2 °2θ.

TABLE 1

Crystallographic Parameters of Three $TiO_2$ Phases

| | Rutile | Anatase | Brookite |
|---|---|---|---|
| Crystal System | Tetragonal | Tetragonal | Orthorhombic |
| a (Å) | 4.6107 | 3.7971 | 9.2110 |
| b (Å) | 4.6107 | 3.7971 | 5.4720 |
| c (Å) | 2.9732 | 9.5790 | 5.1710 |
| α (°) | 90.0000 | 90.0000 | 90.0000 |
| β (°) | 90.0000 | 90.0000 | 90.0000 |
| γ (°) | 90.0000 | 90.0000 | 90.0000 |
| X-Ray Diffraction Peaks (2θ) | 27.4 ± 0.2° | 25.3 ± 0.2° | 25.3 ± 0.2° |
| | 36.1 ± 0.2° | 37.7 ± 0.2° | 25.7 ± 0.2° |
| | 41.2 ± 0.2° | 48.0 ± 0.2° | 30.8 ± 0.2° |
| | 54.3 ± 0.2° | 54.3 ± 0.2° | 36.1 ± 0.2° |
| | 56.5 ± 0.2° | 62.6 ± 0.2° | 48.0 ± 0.2° |
| | 68.9 ± 0.2° | | |

In some aspects, the titanation of the silica support is performed in the liquid phase. In some embodiments, the titanium source is dissolved in an inert solvent. In some embodiments, the titanium source is used neat (i.e. without a solvent). In some embodiments, the inert solvent is a hydrocarbon$_{(C1-12)}$. In some embodiments, the inert solvent is an arene$_{(C1-12)}$. Some non-limiting examples of inert solvent include benzene, toluene, hexane, or heptane. In some embodiments, the inert solvent is toluene. In other aspects, the titanation of the silica support is performed in the vapor phase.

In some aspects, any deposition method may be used to deposit titanium on the silica support. In some embodiments, the titanium precursor is dissolved in a solvent then added to the silica support. In some embodiments, the titanium precursor is dissolved in a solvent containing the silica support. In some embodiments, the deposition of the titanium precursor on the solid support is carried out for a time period sufficient to cause the titanium to deposit within the pore volume and entire surface area of the silica support. In some embodiments, if a solvent is used to assist in the deposition of the titanium on the solid support, the solvent may be removed using an elevated temperature and/or a reduced pressure. In some embodiments, the method further comprises decanting, filtration, or washing. In some embodiments, the method further comprises washing the metal deposited silica support. In other embodiments, the method further comprises not washing the titanated silica support.

In some aspects, the catalyst is calcinated at a temperature from about 100° C. to about 1000° C. In some embodiments, the catalyst is calcinated at a temperature from about 600° C. to about 800° C. In some embodiments, the catalyst is calcinated at a temperature from about 600° C. to about 700° C. In some aspects, the catalyst is calcinated at a temperature for a time period for about 0.5 hours to about 24 hours.

After the calcination, the catalyst may be, in some aspects, washed with a solvent. In some embodiments, the solvent is an alcohol, water, or other solvent which contains at least one free hydroxyl group. In some embodiments, the catalyst is washed at an elevated temperature. In some embodiments, the catalyst is washed at ambient temperature. In some embodiments, the temperature is greater than 50° C. In some embodiments, the temperature is from about 50° C. to about 100° C. In some embodiments, the catalyst is washed for a time period from about 0.1 hours to about 2 hours. Without being bound by any theory, the washing step converts any reactive titanium halide bonds into less reactive titanium hydroxide, alkoxide or oxide bonds.

C. Silylation of the Catalyst

In another aspect of the present disclosure, the catalyst is reacted with a silylating agent. In some embodiments, the silylating agent is selected from organosilanes, organosilylamines, and organosilazanes. In some embodiments, the silylating agent is an organosilane$_{(C\leq 24)}$ with from one to three aliphatic, aromatic, or a substituted version of either of these groups. In some embodiments, the organosilane$_{(C\leq 24)}$ is an organosilane with at least one halo substituent and between 1 and 3 aliphatic, aromatic or a substituted version of either of these groups. In other embodiments, the silylating agent is an organodisilazane$_{(C\leq 24)}$. In some embodiments, the organodisilazane$_{(C\leq 24)}$ is $R_3SiNHSiR_3$, wherein each R is independently selected from an aliphatic, aromatic, or a substituted version of either of these groups. In particular, the R is an aliphatic group with between $C_1$-$C_6$ carbon atoms. For example, hexamethyldisilazane may be used to silylating the washed titanated silica support.

II. METHODS OF PREPARING A CATALYST

In some aspects, the catalyst is prepared using one or more steps including drying of the silica support, titanation of the silica support, and calcination of the titanated silica support. In some embodiments, the titanated silica support is also washed. In some embodiments, the titanated silica support is also reacted with a silylating agent. In some embodiments, the titanated silica support is washed and reacted with a silylating agent. In some aspects, the catalyst compositions described herein are prepared using methods comprising:
  (a) obtaining a silica support with a surface area greater than 800 m²/g and pore volume greater than 1.0 cm³/g;
  (b) drying the silica support;
  (c) depositing titanium from a titanium source neat, in the vapor phase, or dissolved in a solvent on the silica support;
  (d) calcinating the titanated silica support; and
  (e) washing the titanated silica support with water or an alcohol$_{(C\leq 12)}$;

whereby the method produces a catalyst composition, wherein at least 0.1 wt. % of the titanium dioxide phase is in a brookite form. The methods may further comprise reacting the titanated silica support with a silylating agent. In some embodiments, the silylating agent is hexamethyldisilazane. In some embodiments, the silica support is dried at a temperature from about 100° C. to about 850° C. for a time period from about 1 hour to about 48 hours. The titanium sources that may be used in the methods described herein include titanium alkoxides, titanium alkoxide halides, or titanium halides. In some embodiments, the titanium is deposited in the vapor phase by vaporizing the titanium source in a carrier gas at a temperature from about 25° C. to about 800° C. In other embodiments, the titanium is deposited in the solution phase using the titanium source dissolved in an arene$_{(C\leq 12)}$ or alkane$_{(C\leq 12)}$ solvent. In some embodiments, the titanated silica support is calcinated at a temperature from about 300° C. to 800° C. The methods may further comprise drying the titanated silica support after washing with water or an alcohol$_{(C\leq 12)}$.

A. Drying of the Silica Support

In some aspects, the silica support is dried at an elevated temperature. In some embodiments, the drying removes absorbed solvents or water from the silica support. In some embodiments, the elevated temperature is greater than 100° C. In some embodiments, the elevated temperature is from about 100° C. to about 850° C. In some embodiments, the elevated temperature is from about 120° C. to about 400° C. In some embodiments, the elevated temperature is from about 150° C. to about 300° C. Additionally, the drying of the silica support, in some embodiments, comprises drying the silica support for a time period from about 1 hour to about 48 hours. In some embodiments, the time period is from about 2 hours to about 24 hours.

B. Titanation of the Silica support

In some aspects, the silica support is reacted with a titanium source to deposit titanium species on the silica support. In some embodiments, the titanium source is a titanium alkoxide, a titanium halide, or a titanium compound with a mixture of alkoxide or halide anions or ligands. In some embodiments, the titanium source comprises a titanium atom in the +4 oxidation state. In some embodiments, the titanium source is titanium tetrachloride.

In some aspects, the titanation of the silica support is performed in the vapor phase. In some embodiments, the titanium source is prepared in a gaseous phase. In some embodiments, the vapor phase titanation of the silica support is at a temperature from about ambient temperature to about 850° C. In some embodiments, the gaseous phase titanium source is diluted in an inert gas. In some embodiments, the inert gas acts as a carrier for the gaseous phase titanium source. In some embodiments, the inert gas is a noble gas or nitrogen.

In some aspects of the present disclosure, the titanium metal is deposited by dissolving the titanium source in a solvent. In some embodiments, the solvent that the titanium source is dissolved in is an organic solvent selected from an aliphatic hydrocarbon or an aromatic hydrocarbon. In some embodiments, the solvent does not have oxygen atoms. In some embodiments, the organic solvent further comprises a halogen atom. In some embodiments, the solvent is essentially free of water. In some embodiments, the solvent is anhydrous. In some embodiments, the solvent contains less than about 500 ppm of water. In some embodiments, the amount of water present in the deposition solvent is less than 100 ppm of water. In some embodiments, water is added after the deposition of the metal onto the silica support. In some embodiments, water is specifically excluded from the reaction mixture until after the deposition of the silica support with the metal. In some embodiments, the titanium source is dissolved in a solvent with a concentration of the titanium source from about 0.01 M to about 1.0 M.

In some embodiments, the catalyst contains tetrahedrally coordinated titanium sites. In some embodiments, the catalyst contains titanium as an oxide in one or more polymorphic forms. In some embodiments, the titanium on the catalyst is in a brookite form. In some embodiments, the catalyst contains titanium oxide phase in the brookite, rutile, and anatase polymorphic forms. In some embodiments, the catalyst contains titanium in two polymorphic forms wherein one polymorphic form is the brookite form and the other form is selected from the rutile and anatase polymorphic form.

C. Calcination of Titanated Silica Support

In some aspects, the titanated silica support is calcinated at an elevated temperature. In some embodiments, the elevated temperature is from about 100° C. to about 1,000° C. In some embodiments, the elevated temperature is from about 300° C. to about 800° C. In some embodiments, the elevated temperature is from about 600° C. to about 800° C.

In some aspects, a gradual increase in the temperature of the catalyst is used. In some embodiments, the metal deposited silica support is heated to 100° C. for about 15 minutes, then to 250° C. for about 15 minutes, and then heated to 700° C. for about 2 hours. In some embodiments, the calcination is performed under an inert atmosphere such as nitrogen or a noble gas. In some embodiments, the calcination is performed under an inert gas and then in air. Without being bound by any theory, the calcination completes the reaction of the titanium precursor with the silica surface and removes excess titanium and/or hydrogen chloride from the catalyst.

In some aspects, the catalyst may further comprise calcination the titanated silica support. In some embodiments, the calcination of the titanated silica support is carried out in an atmosphere which comprises oxygen. In other embodiments, the calcination of the metal deposited silica support is carried out in the absence of oxygen. In some embodiments, the calcination of the titanated silica support is carried out in an inert gas. Some non-limiting examples of inert gases include nitrogen and the noble gases such as argon and helium.

D. Washing and Silylation of the Titanated Silica Support

In some aspects, the titanated silica support is washed with a hydroxyl containing solvent. In one embodiment, the hydroxyl containing solvent is water. In some embodiments, the hydroxyl containing solvent is an alcohol$_{(C1-18)}$ or water. Without being bound by any theory, the washing of the titanated silica support replaces titanium halide bonds with titanium hydroxide, titanium alkoxide or titanium oxide bonds. In some embodiments, the hydroxyl containing solvent is an alcohol$_{(C1-18)}$. In some embodiments, the titanated silica support is washed with the hydroxyl containing solvent at ambient temperature.

In some aspects, the method comprises drying the washed titanated silica support. In some embodiments, the washed titanated silica support is dried at an elevated temperature. In some embodiments, the temperature is greater than 50° C. In some embodiments, the elevated temperature is from about 50° C. to about 200° C. In some embodiments, the elevated temperature is from about 100° C. to about 150° C. In some embodiments, the washed titanated silica support is dried under a stream of an inert gas. In some embodiments, the washed titanated silica support is dried for a time period from about 0.1 hours to about 2 hours. In some embodiments, the washed titanated silica support is dried for a time period from about 1 hour to about 4 hours. In some embodiments, the time period is about 2 hours.

In some aspects, the washed titanated silica support is reacted with a silylating compound selected from any known silylating compound. In some embodiments, the silylating compound is a disilazane. In some embodiments, the silylating compound is selected from (Me$_3$Si)$_2$NH or (RMe$_2$Si)$_2$NH wherein the R is an aliphatic compound, an aromatic compound, or a substituted version of any of these groups. In some embodiments, R is an alkyl, alkenyl, or aryl group. Without being bound by any theory, the silylating compound reacts with hydroxyl groups on the titanium to form Ti—OSiR$_3$ groups.

In some embodiments, the washed titanated silica support is silylated for a time period from about 0.1 hours to about 6 hours. Without being bound by any theory, the time period need to react the washed metal deposited silica support varies depending on the temperature, pressure, and silylating agent. In some aspects, the silylation of the washed titanated silica support occurs in the liquid phase. In some embodiments, the silylating agent is dissolved in a solvent. In other embodiments, the silylating agent is added to the washed titanated silica support neat (i.e. without additional solvent). In some embodiments, the silylating agent is reacted with the washed titanated silica support in the vapor phase. In some embodiments, treating the washed titanated silica support with the silylating agent at an elevated temperature. In some embodiments, the temperature is from about 80° C. to about 450° C. In some embodiments, the temperature used in the silylation reaction is from about 80° C. to about 300° C.

In some aspects, the amount of silylating agent added to the silica support is from about 1 wt. % to about 75 wt. %. In some embodiments, the amount of silylating agent is from about 2 wt. % to about 50 wt. %. In some embodiments, the washed metal deposited silica support is reacted with the silylating agent once. In other embodiments, the washed metal deposited silica support is reacted with the silylating agent more than once. Such silylating reactions can be carried out in a batch, semi-continuous, or continuous manner.

III. METHODS OF EPOXIDATION USING A CATALYST

In some aspects of the present disclosure, the catalysts described herein may be used in the production of epoxides from an olefin. In some embodiments, the catalyst may be used in either batch or continuous epoxidation methods. In some embodiments, utilizing the catalyst in epoxidation methods leads to higher conversion of the reaction mixture such as higher yield. In some aspects, the present disclosure provides methods of preparing an epoxide comprising:

(a) admixing an olefin$_{(C2-12)}$ and an oxidizing agent; and
(b) contacting the olefin$_{(C2-12)}$ and oxidizing agent with a catalyst described herein under conditions sufficient to epoxidize an olefin$_{(C2-12)}$.

In some embodiments, the oxidizing agent is an organic hydroperoxide, such as tert-butyl hydroperoxide, cumene hydroperoxide, or ethylbenzene hydroperoxide. These methods may use olefin such as propylene.

In some aspects, the epoxidation method further comprises an oxidizing agent. In some embodiments, the oxidizing agent is a hydroperoxide. In some embodiments, the hydroperoxide is an alkylhydroperoxide. In some embodiments, the alkyl group has from 1 to about 12 carbon atoms. In some embodiments, the alkyl group is tert-butyl. In other embodiments, the hydroperoxide is an aralkylhydroperoxide. In some embodiments, the aralkyl group has from 1 to about 24 carbon atoms. In some embodiments, the aralkyl group has from about 1 to about 12 carbon atoms. In some embodiments, the aralkyl group is ethylbenzyl or cumyl.

In some aspects, the epoxidation method comprises adding an olefin to the reaction mixture. In some embodiments, the olefin has from about 1 to about 24 carbon atoms. In some embodiments, the olefin has from about 1 to about 12 carbon atoms. In some embodiments, the olefin comprises at least one non-aromatic double bond. In some embodiments, the olefin is propylene. In some embodiments, the olefin may also be substituted with one or more other groups including hydroxyl or halide groups.

In some aspects, the ratio of olefin to oxidizing agent is a molar ratio from about 1:1 to about 20:1, including about 10:1 to about 12:1.

In some embodiments, the epoxidation reaction occurs in the liquid phase. In some embodiments, the liquid phase comprises one or more solvents or inert diluents. In some embodiments, the solvent is the hydrocarbon precursor of the hydroperoxide either the corresponding alkane or alcohol. In a non-limiting example, if the hydroperoxide is tert-butyl hydroperoxide the solvent that is optionally used is tert-butanol.

In some aspects, the epoxidation reaction is modified by adjusting the pressure and/or the temperature. In some embodiments, the epoxidation reaction is carried out at a temperature from about 25° C. to about 200° C. In some embodiments, the temperature is from about 50° C. to about 160° C. In some embodiments, the temperature is from about 70° C. to about 140° C. In some embodiments, the epoxidation reaction is carried out at a pressure from about ambient pressure to greater than atmospheric pressure. In some embodiments, the pressure is from about 20 psi to about 1500 psi. In some embodiments, when propylene used as the substrate, the pressure is from 400 psi to 1000 psi.

In some aspects, the epoxidation reaction comprises multiple different phases including some of the reactants in the gaseous and other reactants in the liquid phase with the catalyst in the solid phase. In some embodiments, the epoxidation reaction comprises both reactants in the liquid phase and the catalyst in the solid phase such that the catalyst in the reaction mixture is used heterogeneously. In some embodiments, the epoxidation reaction is performed in any commercially useful reactor. In certain embodiments, the reactor is selected from a continuous or batch process reactor. Some non-limiting examples of reactors include a fixed bed or a slurry reactor. When any of these reactors are used, the reaction may further comprise separating the reactants and catalyst from the products. In some embodiments, the epoxidation reaction comprises a fractional distillation, selective extraction, filtration, and/or a similar separation technique. In certain embodiments, any unreacted reactants, the solvent, and/or the catalyst can be reused in the epoxidation reaction.

IV. PROCESS SCALE-UP

The above methods can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2012), which is incorporated by reference herein.

V. DEFINITIONS

When used in the context of a chemical group: "alkoxide" refer to an oxygen substituent which has a single negative charge and is attached to an aliphatic or aromatic hydrocarbon. Some non-limiting examples of alkoxides include methoxide, ethoxide or phenoxide. The term "halide" means a halogen atom formulated as an anion bearing a single negative charge. Any undefined valency on an atom of a structure shown in this application implicitly represents a hydrogen atom bonded to that atom.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C \leq 8)}$" or the class "alkene$_{(C \leq 8)}$" is two. For example, "alkoxy$_{(C \leq 10)}$" designates those alkoxy groups having from 1 to 10 carbon atoms. (Cn-n') defines both the minimum (n) and maximum number (n') of carbon atoms in the group. For example, "alkyl$_{(C2-10)}$" designates those alkyl groups having from 2 to 10 carbon atoms.

The term "saturated" when used to modify a compound or an atom means the compound or atom has no carbon-carbon double and no carbon-carbon triple bonds, except as noted below. When the term "saturated" is used in the context of a solution and a solute, it means that no more of that substance can be dissolved in that solution.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "alkyl" refers to a monovalent saturated aliphatic group with a carbon atom as the point of attachment, a linear or branched acyclic structure, and no atoms other than carbon and hydrogen. An "alkane" refers to the class of compounds having the formula H—R, wherein R is alkyl as this term is defined above.

The term "alkenyl" refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. The terms "alkene" or "olefin" are synonymous and refer to the class of compounds having the formula H—R, wherein R is alkenyl as this term is defined above. A "terminal alkene" refers to an alkene having just one carbon-carbon double bond, wherein that bond forms a vinyl group at one end of the molecule.

The term "aryl" refers to a monovalent unsaturated aromatic group with an aromatic carbon atom as the point of attachment, said carbon atom forming part of a one or more six-membered aromatic ring structure, wherein the ring atoms are exclusively carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. An "arene" refers to the class of compounds having the formula H—R, wherein R is aryl as that term is defined above. Benzene and toluene are non-limiting examples of arenes.

The term "arylalkene" when used without the "substituted" modifier refers to the class of compounds having the formula aryl-alkenyl, in which the terms aryl and alkenyl are each used in a manner consistent with the definitions provided above.

The term "alkoxy" refers to the group —OR, in which R is an alkyl, as that term is defined above. The term "alcohol" corresponds to an alkane, as defined above, wherein at least one of the hydrogen atoms has been replaced with a hydroxy group.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes a variation of error for the device, the method being employed to determine the value, or the variation that exists among the study subjects. The term "about" when used in the context of epoxidation process conditions is used to imply the natural variation of conditions and represent a variation of plus or minus 5% of the measurement. In some embodiments, the variation is plus or minus 1% of the measurement. When the term "about" is used in the context of X-ray diffraction peaks, the term is used to express variation in the peak position of ±0.2 °2θ.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing solely those one or more steps and also covers other unlisted steps.

The term "epoxide" refers to a class of compounds of the formula:

wherein $R_1$, $R_2$, and $R_3$ are each independently hydrogen, alkyl, and $R_4$ is hydrogen, alkyl, or aryl. An "epoxidation reaction" is a reaction which leads to generation of an epoxide on the molecule. A common epoxidation reaction results from converting an alkene or aralkene functional group within a molecule into an epoxide group.

The modifier "inert" indicates that a component, chemical compound, or chemical group does not react or change (e.g., decompose) under the conditions of a reaction or process.

A "method" is series of one or more steps undertaking lead to a final product, result or outcome. As used herein, the word "method" is used interchangeably with the word "process".

The term "organosilicate" refers to the group —$OSiR_3$, wherein each R is independently hydrogen, an aliphatic group such as an alkyl group or an alkenyl group, or an aromatic group such as an aryl group.

The term "silica support" refers to a solid material that has silica has the main constituent. In some embodiments, the material further comprises other non-siliceous components, e.g., alumina or magnesium chloride. When the support is used as part of catalyst compositions for use in catalytic reactions, the support may be inert or participate in the catalytic reactions.

The term "titanium" refers to a titanium atom in any oxidation state. In some aspects, the term "titanium" refers to a titanium atom which has an oxidation state of 0, +1, +2, +3, and +4. In some embodiments, the titanium has a +4 oxidation state.

The term "titania" refers to titanium dioxide of the formula: $TiO_2$.

The abbreviation "wt. %" corresponds to weight percent.

The above definitions supersede any conflicting definition in any reference that is incorporated herein. The fact that certain terms are defined, however, should not be considered as indicative that any term that is undefined is indefinite. Rather, the terms used herein are believed to describe the present technology in terms such that one of ordinary skill can appreciate the scope and practice the technology.

VI. EXAMPLES

The following examples are included to demonstrate certain embodiments of the technology. It should be appreciated by those of skill in the art that the techniques disclosed in the examples which follow represent techniques discovered by the inventor to function well in the practice of the technology, and thus can be considered to constitute certain modes for its practice. However, those of skill in the art should, in light of the present disclosure, appreciate that many changes can be made in the specific embodiments which are disclosed and still obtain a like or similar result without departing from the spirit and scope of the technology.

Example 1: Preparation of Catalyst Compositions

Comparative Catalyst Composition C1 is prepared according to Example 1-A described in U.S. Pat. No. 6,011,162 using Grace V-432 silica having a surface area of 320 m²/g and a pore volume of 1.1 mL/g. The catalyst has a Ti content of 5.0%. The catalyst exhibits A(batch)=4.90 g/g/h and A(cont)=7.88 h$^{-1}$@60° C. after 50 h on stream. The brookite form of $TiO_2$ is not present in the sample according to its powder X-ray diffraction spectrum shown in FIG. 1.

Catalyst Composition N1. 2.03 g of silica support CS2010 of PQ corporation (surface area 969 m²/g, pore volume 2.21 mL/g, average pore diameter 91 Å, and particle size 0.7-1.2 mm) was dried at 200° C. for 15 h in a quartz column in a 100 mL/min $N_2$ flow. The dried silica was impregnated in the column with 8 mL of 1M $TiCl_4$ solution in toluene. After 30 minutes the temperature was raised to 100° C. for 15 minutes (min), then 250° C. for 15 min and finally to 700° C. for 2 hours (h) under flowing $N_2$. The catalyst was cooled to ambient temperature and washed with 40 mL of methanol, followed by drying 2 h at 200° C. The catalyst was silylated by adding 1.2 mL of hexamethyldisilazane (HMDS) at 170-200° C. and kept at that temperature for 30 min in $N_2$ flow. The catalyst has a Ti content of 6.90%. The catalyst exhibits A(batch)=7.01 g/g/h and A(cont)=9.65 h$^{-1}$ at 50° C. after 100 h on stream. The brookite form of $TiO_2$ is present in the sample according to its powder X-ray diffraction spectrum shown in FIG. 1.

Catalyst Composition N2. 2.06 g of silica support CS2010 of PQ Corporation (surface area 969 m²/g, pore volume 2.21 mL/g, average pore diameter 91 Å and particle size 0.7-1.2 mm) was dried at 200° C. for 15 h in a quartz column in a 100 mL/min $N_2$ flow. The dried silica was treated with a vaporized $TiCl_4$ (0.8 mL) at 200° C. and kept at this temperature for 30 min then calcined at 800° C. for 1 h under flowing $N_2$. The catalyst was cooled to ambient temperature and washed with 40 mL of methanol, followed by drying 2 h at 200° C. The catalyst was silylated by adding 1.3 mL of hexamethyldisilazane (HMDS) at 170-200° C. and kept at that temperature for 30 min in $N_2$ flow. The catalyst exhibits A(batch)=7.28 g/g/h and A(cont)=9.23 h$^{-1}$ at 47° C. after 60 h on stream. The brookite form of $TiO_2$ is present in the sample according to its powder X-ray diffraction spectrum shown in FIG. 1.

Catalyst Composition N3. 10.06 g of silica support CS2010 of PQ Corporation (surface area 969 m²/g, pore volume 2.21 mL/g, average pore diameter 91 Å and particle size 0.7-1.2 mm) was dried at 200° C. for 50 h in a quartz column in a 100 mL/min $N_2$ flow. The dried silica was transferred into a flask, followed by addition of 48 mL of toluene. 3.3 mL of $TiCl_4$ was slowly and evenly added to the slurry with periodic mixing and heated on an oil bath at 100°

C. for 1 hour. Part of the liquid (10 mL) was removed and the content was heated to 150° C. in a $N_2$ stream for 1 h then to 200° C. for 30 min to dry. The solid was transferred under $N_2$ to a calcination tube and calcined in $N_2$ at 650° C. for 2 h and an additional 1 h in air. The calcined catalyst was washed with 180 mL of methanol, followed by drying for 2 h at 190° C. The catalyst bed was silylated by adding 6 mL of hexamethyldisilazane (HMDS) at 170° C. and kept at that temperature for 30 min in $N_2$ flow. The catalyst has a Ti content of 5.94%. The catalyst exhibits A(batch)=7.51 g/g/h and A(cont)=9.86 $h^{-1}$ at 47° C. after 50 h on stream. The brookite form of $TiO_2$ is present in the sample according to its powder X-ray diffraction spectrum shown in FIG. 1.

Figure 1:
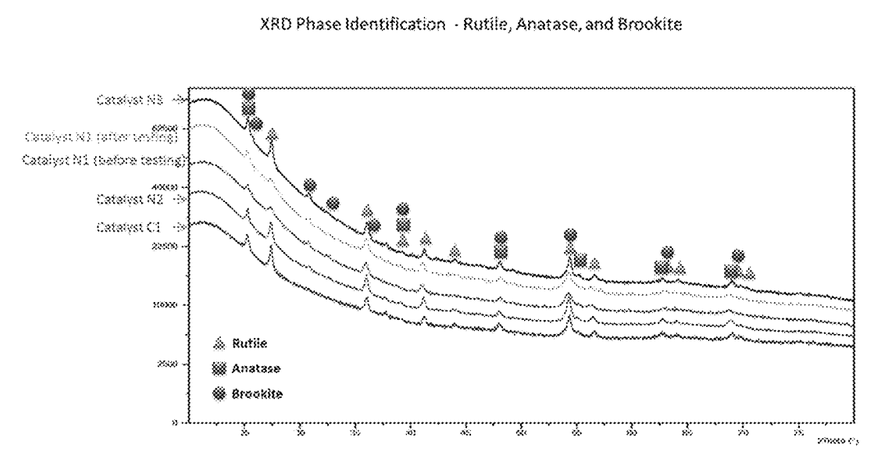
FIG. 1 provides a graph showing the powder x-ray diffraction spectra of non-limiting examples of catalyst compositions provided herein, including comparative catalyst composition. Several of the peaks are attributed to specific forms of titanium dioxide.

Example 2: Characterization of Catalyst Composition Using Powder X-Ray Diffraction Diffraction measurements were performed with a PANalytical X'Pert PRO MPD instrument using Ni-filtered Cu Kα radiation. A 2θ angle scan range from 20° to 80°, a scanning step size of 0.0167°, a time per step of 2500 seconds and a PIXcel detector were used. Samples were measured in a reflection configuration (Bragg-Brentano geometry). Diffraction patterns of anatase, rutile, and brookite $TiO_2$ powders were compared with reference in the ICDD PDF4+ 2013 database. FIG. 1 shows the X-ray diffraction (XRD) patterns for the catalysts.

As can be seen in FIG. 1, the catalyst compositions N1-N3 comprise titanium dioxide in a brookite form. This form was not present in comparative catalyst composition C1.

Example 3: Catalytic Performance in Batch and Continuous Epoxidation Experiments a. Batch Epoxidation of 1-Octene Using TBHP Oxidate An aliquot (14 mL) of a 1-octene solution of 41% tert-butylhydroperoxide (TBHP) in tert-butyl alcohol (4.4 wt % TBHP in 1-octene) is placed in a round-bottom flask equipped with a magnetic stir bar. The mixture is heated to 80° C. under nitrogen. The epoxidation reaction is started by adding a catalyst sample of specified weight to start the reaction. The reaction continues for 1 h, after which a sample is removed from the flask using a needle with an in-line filter. TBHP content before and after the test is determined by iodometric titration, and the percent of conversion is calculated. Based on these conversion values and catalyst amount the activity of the catalyst [A(batch)] is quantified as grams of TBHP reacted per gram of catalyst per hour under the above specified conditions.

b. Continuous Propylene Epoxidation

A small, continuous unit is used to compare catalyst performance under the following conditions: catalyst amount: 1.35 g; pressure: 850 psig; propylene feed rate: 10 g/h (19.2 mL/h); TBHP feed rate: 4.3 g/h (5.0 mL/h); total volumetric flow: 19.6 mL/h; molar ratio of propylene to TBHP: 12:1 and linear hourly space flow velocity (LHSV) of 6.3 $h^{-1}$. The catalyst bed temperature was adjusted to reach about 70% TBHP conversion. The catalyst activity at a certain time on stream an certain catalyst bed temperature is was expressed as A(cont)=−LHSV*(1−X), where X is the fraction of reacted TBHP.

c. Comparison of Epoxidation Results

The catalysts compositions N1-N3, all of which comprise the brookite form of $TiO_2$, show increased activity in both batch and continuous epoxidation reactions.

Catalyst Composition C1 exhibits A(batch)=4.90 g/g/h and A(cont)=7.88 $h^{-1}$ at 60° C. after 50 h on stream.

Catalyst Composition N1 exhibits A(batch)=7.01 g/g/h and A(cont)=9.65 $h^{-1}$ at 50° C. after 100 h on stream.

Catalyst Composition N2 exhibits A(batch)=7.28 g/g/h and A(cont)=9.23 $h^{-1}$ at 47° C. after 60 h on stream.

Catalyst Composition N3 exhibits A(batch)=7.51 g/g/h and A(cont)=9.86 $h^{-1}$ at 47° C. after 50 h on stream.

All of the compositions and methods disclosed and claimed herein can be made and executed without undue experimentation in light of the present disclosure. While the compositions and methods of this disclosure have been described in certain embodiments, it will be apparent to those of skill in the art that variations may be applied to the compositions and methods as well as in the steps or in the sequence of steps of the method described herein without departing from the concept, spirit, and scope of the disclosure. More specifically, it will be apparent that certain agents which are chemically related may be substituted for the agents described herein while the same or similar results would be achieved. Any such similar substitutes and modifications apparent to those skilled in the art are deemed to be within the spirit, scope and concept of the technology as defined by the appended claims.

REFERENCES

The following references to the extent that they provide exemplary procedural or other details supplementary to those set forth herein, are specifically incorporated herein by reference.
1) U.S. Pat. No. 6,011,162
2) U.S. Pat. No. 6,114,552
3) WIPO PCT Pub. No. WO 2011/161412
4) WIPO PCT Pub. No. WO 2012/010491
5) Anderson, N. G., *Practical Process Research & Development—A Guide for Organic Chemists*, 2nd ed., Academic Press, New York, 2012.

What is claimed is:

1. A catalyst composition comprising:
   (a) titanium, wherein a part of the titanium is present as a titanium dioxide phase and at least 0.1 wt. % of the titanium dioxide phase relative to the total titanium dioxide phase is in a brookite form; and
   (b) a silica support comprising a pore volume greater than 1.0 $cm^3/g$,
   wherein the titanium has been deposited on the silica support wherein the catalyst composition has a powder X-ray diffraction spectra comprising peaks at about 25.3, 25.7, 30.8, 36.1, and 48.0 .degree.2.theta.

2. The catalyst composition of claim 1, wherein the brookite form of the titanium dioxide phase is present in an amount from about 0.1 wt. % to about 50 wt. % of the titanium dioxide phase relative to the total titanium dioxide phase.

3. The catalyst composition of claim 1, wherein the silica support comprises amorphous silica having:
   (a) a surface area greater than 800 $m^2/g$.

4. The catalyst composition of claim 1, wherein the amount of the total titanium dioxide phase is from about 1 wt. % to about 8 wt. % of the catalyst composition.

5. The catalyst composition of claim 1, further comprising a plurality of organosilicate$_{(C1-24)}$ groups on the surface of the catalyst composition.

6. The catalyst composition of claim 5, wherein the organosilicate$_{(C1-24)}$ group is —OSi(CH$_3$)$_3$.

7. A method for producing the catalyst composition of claim 1, comprising:

(a) obtaining a silica support, wherein the silica support comprises amorphous silica having a surface area greater than 800 m²/g and pore volume greater than 1.0 cm³/g;
(b) drying the silica support to produce a dried silica support;
(c) depositing a titanium-containing reagent on the dried silica support to produce a titanium-treated silica support;
(d) calcining the titanium-treated silica support to produce a titanated silica support; and
(e) washing the titanated silica support with water or an alcohol$_{(C1-12)}$ to form a washed titanated silica support; wherein at least 0.1 wt. % of the titanium dioxide phase relative to the total titanium dioxide phase is in a brookite form.

8. The method of claim 7, wherein the silica support is dried at a temperature from about 100° C. to about 850° C. for a time period from about 1 hour to about 48 hours.

9. The method of claim 7, wherein the titanium-containing reagent is titanium(IV) alkoxide, titanium(IV) halide, or a mixed titanium(IV) alkoxide halide.

10. The method of claim 9, wherein the titanium(IV) halide is TiCl$_4$.

11. The method of claim 10, wherein the TiCl$_4$ is deposited to the dried silica support as a liquid, as a gas, or as part of a solution, wherein the solution further comprises an aromatic or aliphatic solvent.

12. The method of claim 7, wherein the titanium-containing reagent is deposited in the vapor phase at temperature from about 25° C. to about 800° C.

13. The method of claim 7, wherein the titanium-treated silica support is calcined at a temperature from about 300° C. to 800° C.

14. The method of claim 7, wherein the method further comprises drying the washed titanated silica support.

15. The method of claim 7, wherein the method further comprises reacting the washed titanated silica support with a silylating agent.

16. A method for producing an epoxide comprising:
(a) admixing an olefin$_{(C2-12)}$ and an oxidizing agent to form a reaction mixture; and
(b) contacting the olefin$_{(C2-12)}$ and oxidizing agent with a catalyst composition of claim 1 under conditions sufficient to produce an epoxide$_{(C2-12)}$.

17. The method of claim 16, wherein the oxidizing agent is an organic hydroperoxide.

18. The method of claim 17, wherein the organic hydroperoxide is tert-butyl hydroperoxide, cumene hydroperoxide, or ethylbenzene hydroperoxide.

19. The method of claim 16, wherein the olefin is propylene.

* * * * *